(12) United States Patent
Abecasis

(10) Patent No.: US 10,857,415 B2
(45) Date of Patent: Dec. 8, 2020

(54) MULTIFUNCTIONAL THERAPEUTIC WORKOUT ENHANCEMENT BRACE

(71) Applicant: Jordan Alexander Abecasis, Coral Springs, FL (US)

(72) Inventor: Jordan Alexander Abecasis, Coral Springs, FL (US)

( * ) Notice: Subject to any disclaimer, the term of this patent is extended or adjusted under 35 U.S.C. 154(b) by 155 days.

(21) Appl. No.: 16/119,965

(22) Filed: Aug. 31, 2018

(65) Prior Publication Data

US 2019/0060700 A1 Feb. 28, 2019

Related U.S. Application Data

(60) Provisional application No. 62/552,727, filed on Aug. 31, 2017.

(51) Int. Cl.
| | | |
|---|---|---|
| A63B 21/00 | (2006.01) |
| A63B 23/12 | (2006.01) |
| A63B 71/08 | (2006.01) |
| A63B 21/16 | (2006.01) |
| A61F 5/01 | (2006.01) |

(52) U.S. Cl.
CPC ........ *A63B 21/4017* (2015.10); *A61F 5/0118* (2013.01); *A63B 21/16* (2013.01); *A63B 23/1245* (2013.01); *A63B 71/08* (2013.01); *A63B 2209/10* (2013.01); *A63B 2225/09* (2013.01)

(58) Field of Classification Search
CPC . A63B 21/4017; A63B 23/1245; A63B 71/08; A63B 21/16; A63B 2209/10; A63B 2225/09; A61F 5/0118
See application file for complete search history.

(56) References Cited

U.S. PATENT DOCUMENTS

| | | | | | |
|---|---|---|---|---|---|
| 4,123,052 | A | * | 10/1978 | Perkins | A61F 5/373 446/26 |
| 4,684,122 | A | * | 8/1987 | Desmond | A63B 71/00 482/105 |
| 4,949,957 | A | * | 8/1990 | Cucchiara | A63B 23/03508 482/102 |
| 5,048,825 | A | * | 9/1991 | Kelly | A63B 21/154 482/904 |
| 5,163,413 | A | * | 11/1992 | Carella | A63B 21/0552 124/88 |
| 5,501,656 | A | * | 3/1996 | Homma | A61H 1/02 601/33 |
| 5,518,480 | A | * | 5/1996 | Frappier | A63B 21/0004 482/124 |

(Continued)

*Primary Examiner* — Sundhara M Ganesan

(57) ABSTRACT

A multifunctional therapeutic workout enhancement brace has a joint-receiving sling, a pair of adjustable cuffs, and a tension-diverting band. The joint-receiving sling is a flexible piece of material that is molded to conform to the shape of the user's joint. The pair of adjustable cuffs are mounted along opposite edges of the joint-receiving sling. Thus, enabling the user to attach the adjustable cuffs to opposite sides of the user's joint. The tension-diverting band is a strip of material that is mounted in between the adjustable cuffs and the joint-receiving sling. Thus positioned, the tension-diverting band transfers forces that are directed toward the user's joint out of the joint-receiving sling and into the adjustable cuffs. Further, the joint-receiving sling, the pair of adjustable cuffs, and the tension-diverting band work in concert to reduce the torque applied to the user's joint during exercise.

4 Claims, 9 Drawing Sheets

(56) References Cited

U.S. PATENT DOCUMENTS

| | | | | |
|---|---|---|---|---|
| 5,626,544 | A * | 5/1997 | Foresto | A63B 21/0552 482/10 |
| 5,848,956 | A * | 12/1998 | Grettner | A61F 5/3738 482/69 |
| 6,168,556 | B1 * | 1/2001 | Saavedra | A63B 21/4019 224/220 |
| 7,325,254 | B1 * | 2/2008 | Edgar | A63B 21/0004 2/102 |
| 7,608,026 | B1 * | 10/2009 | Nicassio | A63B 21/00185 24/265 BC |
| 8,337,371 | B2 * | 12/2012 | Vollmer, Jr. | A63B 23/0355 482/124 |
| 9,066,787 | B1 * | 6/2015 | Price | A61F 5/0106 |
| 9,295,869 | B2 * | 3/2016 | Washington | A63B 21/0442 |
| 2007/0004571 | A1 * | 1/2007 | Gonzalez | A63B 21/0004 482/124 |
| 2008/0026922 | A1 * | 1/2008 | Smith | A63B 21/025 482/124 |
| 2009/0209396 | A1 * | 8/2009 | Ferguson | A63B 21/4017 482/139 |
| 2010/0285936 | A1 * | 11/2010 | Tacker | A63B 21/0602 482/105 |
| 2011/0160025 | A1 * | 6/2011 | Vollmer, Jr. | A63B 23/0355 482/139 |
| 2011/0301718 | A1 * | 12/2011 | Carter | A63B 71/0009 623/57 |
| 2013/0143724 | A1 * | 6/2013 | DeMeo | A63B 21/00185 482/131 |
| 2015/0148204 | A1 * | 5/2015 | Sleppy | A63B 21/4043 482/139 |
| 2015/0209607 | A1 * | 7/2015 | Fields | A63B 21/008 482/112 |
| 2015/0251038 | A1 * | 9/2015 | Bybee | A63B 21/0442 482/124 |
| 2016/0256725 | A1 * | 9/2016 | Verdi | A63B 21/4019 |
| 2017/0140664 | A1 * | 5/2017 | Arnold | A63B 21/00185 |
| 2018/0178050 | A1 * | 6/2018 | Prihar | A63B 21/4017 |
| 2019/0151704 | A1 * | 5/2019 | Littlejohn | A63B 21/0552 |

* cited by examiner

MULTIFUNCTIONAL THERAPEUTIC WORKOUT ENHANCEMENT BRACE

The current application claims a priority to the U.S. Provisional Patent application Ser. No. 62/552,727 filed on Aug. 31, 2017.

FIELD OF THE INVENTION

The present invention relates generally to exercise equipment. More specifically, the present invention is an exercise apparatus designed to redirect tension and provide additional support and versatility during physical activity.

BACKGROUND OF THE INVENTION

Injuries of the glenohumeral joint are a common occurrence in athletes and manual workers. To ensure a balanced exercise routine, individuals focus on incorporating workouts that are designed to engage all areas of the human body. Frequent injuries are the result of doing repetitive motions for extended periods of time (overuse), using improper posture, physical contact, or incorrect usage of equipment. Damage to the musculoskeletal system of the human body requires lengthy recovery times, and in many cases, surgical intervention is required. These types of injuries not only require extended periods of time to heal, but can also be extremely costly, both in terms of the medical care required, but also the fact that the user is more than likely unable to work while receiving treatment. Treatment for such injuries requires in-depth physical therapy, therefore a patient may be restricted to only certain movements for periods at a time, making work (given a manual labor job), or any physical activity very difficult. If the injury is significant, in some cases it can lead to a lifetime of recurring problems, constant pain and an overall decreased quality of life. The use of proper equipment and correct form is strongly encouraged during vigorous exercises routines. Depending on their individual goal, each person adheres to workouts with varying degrees of intensity. While the scope of this invention works throughout the glenohumeral joint, the population of individuals who suffer from neurological and or physical damage to the hand/wrist that cause debilitation of the action of "closing" a hand will now have a plethora of alternative exercises accessible, dramatically increasing the quality of life for those who cannot utilize a hand grip.

Current solutions to this problem, include various braces that are able to increase support during certain movements. The increased support however, usually is very inefficient. Most cable accessories are designed to be used through the use of a hand grip accessory that provide substantial amount of torque onto the glenohumeral joint. There is currently no existing elbow accessory on the market that is designed to relocate cable tension to specific areas of the upper limb. In addition, these products lack the necessary features that allow the user to easily interchange between muscle groups in their workout routine. Proper development of the shoulder girdle requires the individual to go through a range of motions and exercises to strengthen the affected joint area efficiently. Unfortunately, people that sustain hand injuries or suffer from neurological disorders often lose the ability to grip objects, as well as the dexterity in their fingers. Besides daily tasks that become increasingly difficult to manage, working out the upper body can also be problematic. Traditionally, most upper body workouts rely heavily on the ability of the user to hold and grip weights, dumbbells, and barbells. The present invention aims to solve some of the problems by providing a new method utilizing the elbow joint to serve as the location of emphasis for the attachment cables or resistance bands at specific locations. The redirected tension allows users to conduct a variety of motions with reduced torque placed on the glenohumeral joint, as well as an easier point of emphasis for individuals with hand/wrist complications. The tensions applied to the user's body is directly correlated to where the invention is positioned, as anterior, lateral and posterior positioning allows for the magnitude of possible exercises to be controlled. Furthermore, the present invention is able to provide significant advances in shoulder rehabilitation through engagement of the muscles with a lower degree of torque with greater stability via the elbow joint connection, and significant improvements of the life quality in all individuals suffering from hand/wrist complications who once were restricted to certain movements.

People often look for ways to achieve a more balanced workout designed in which utilization of all bodily muscles are utilized. Various equipment may be used depending on the body part that user wants to work out. During physical exercise forces of various degrees of intensity are applied to the joints and the user's muscles. The present invention aims to provide a more complete workout and rehabilitation process by allowing the user to perform and transition between exercises for the chest, shoulder, back, abdominal, or leg muscles through the redirection of cable or elastic tension positioned at the anterior, lateral and posterior locations of the elbow joint. Furthermore, the device provides an alternative workout solution for people with limited hand dexterity, or amputated limbs and extremities. The present invention is an exercise apparatus, designed to redirect tension and pressure of the glenohumeral joint from the user's hands, to the individuals elbow joint, thus redistributing the total magnitude of torque applied to the shoulder during physical strain by decreasing the overall distance of the joint to point of emphasis on the elbow accessory.

DETAIL DESCRIPTIONS OF THE INVENTION

Figure 1:
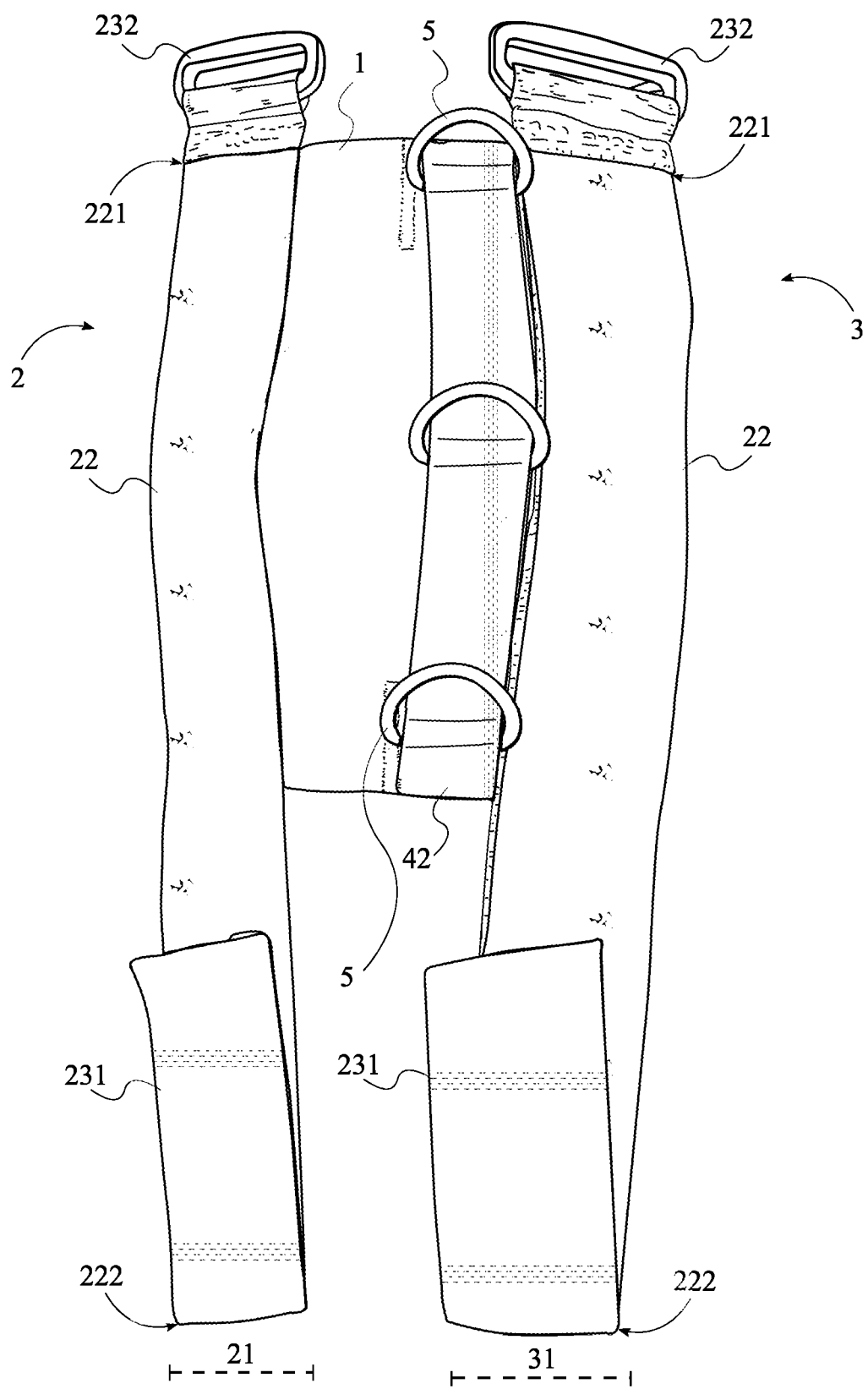
FIG. 1 is a front perspective view of the present invention.

All illustrations of the drawings are for the purpose of describing selected versions of the present invention and are not intended to limit the scope of the present invention.

Referring to FIG. 1 through FIG. 9, the present invention, the multifunctional therapeutic workout enhancement brace, is a therapeutic brace that is designed to be wrapped around a user's elbow while exercising. Once affixed to the elbow, the present invention is designed to enable the user to perform a plurality of hands-free exercises. More specifically, the present invention redistributes the forces placed on the user's shoulder during strenuous activities including, but not limited to, weightlifting, exercising, and playing sports. Preferably, the present invention is designed to be attached to the user's elbow. However, alternative embodiments of the present invention can be attached to various other body parts including, but not limited to, knees, wrists, and ankles. To act as a brace, the present invention comprises a joint-receiving sling 1, at least one first adjustable cuff 2, at least one second adjustable cuff 3, and at least one tension-diverting band 4. The joint-receiving sling 1 is a piece of material that is molded to conform to the shape of the joint, around which the present invention is attached. Preferably, the joint-receiving sling 1 is a semi-rigid member used to support the user's elbow without limiting the user's range of motion. The joint-receiving sling 1 comprises a first lengthwise edge 11 and a second lengthwise edge 12. The first lengthwise edge 11 is positioned opposite to the second lengthwise edge 12 across the joint-receiving sling 1. Accordingly, the joint-receiving sling 1 is shaped to be laterally mounted onto the user's elbow without hindering the elbow from being bent or straightened.

Figure 6:
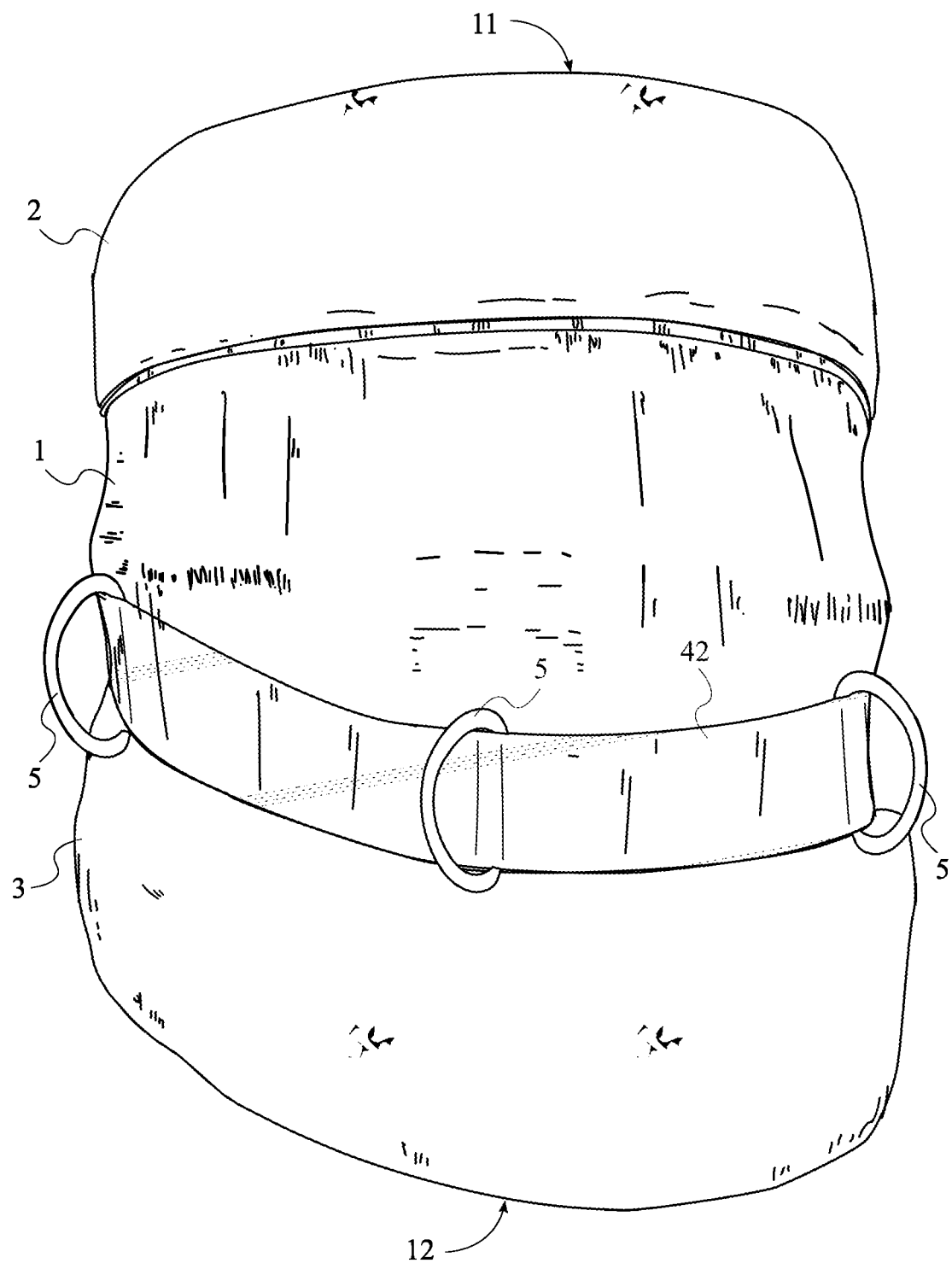
FIG. 6 is a front perspective view of the present invention when the adjustable fastener is engaged.
Figure 7:
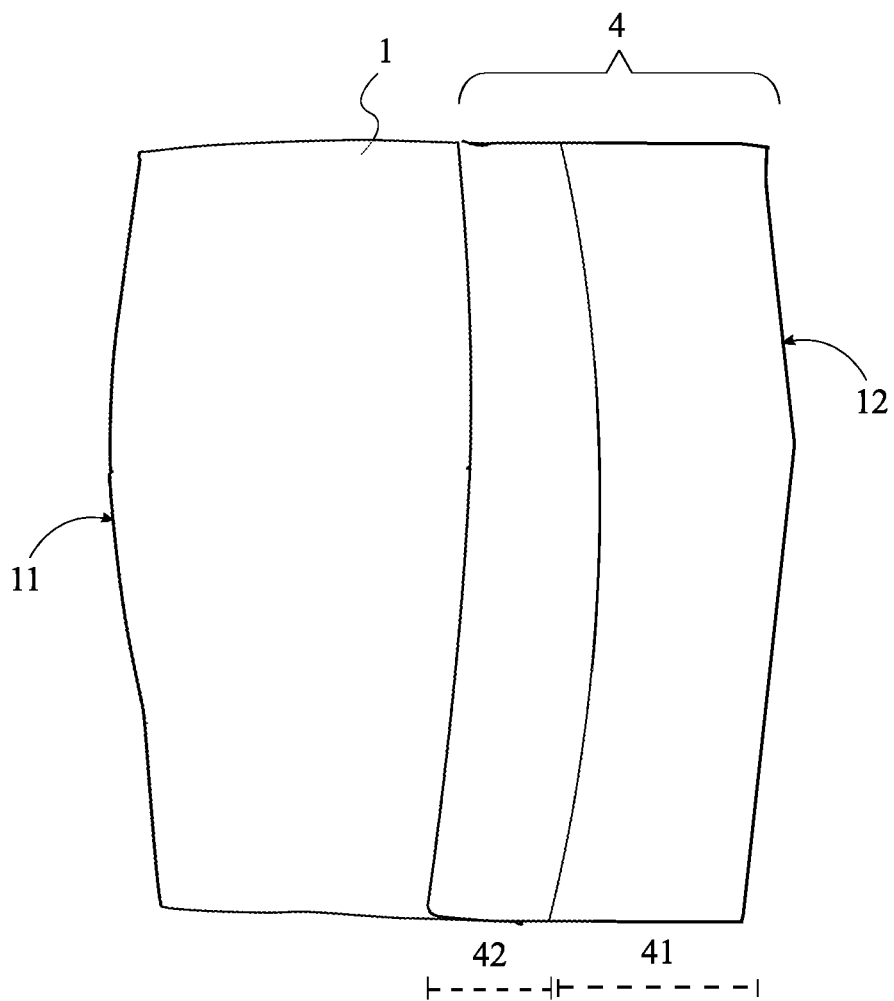
FIG. 7 is a front perspective view of the present invention with the first adjustable cuff and the second adjustable cuff removed.

Referring to FIG. 6 and FIG. 7, the present invention is designed to function as a mounting mechanism that enables external exercise equipment to be attached to the user's elbow. Thus, enabling the present invention to function as a device for rehabilitating a damaged shoulder joint. To achieve this functionality, the present invention employs the first adjustable cuff 2 and the second adjustable cuff 3 as tension-directing members that enable forces exerted by the external exercise equipment to be supported by the bicep and forearm rather than the user's hand. Further, the first adjustable cuff 2 and the second adjustable cuff 3 are designed to incorporate length-adjustable mechanisms that can be resized to accommodate users of varying shape and size. The first adjustable cuff 2 is adjacently connected to the joint-receiving sling 1, along the first lengthwise edge 11. Thus connected, the first adjustable cuff 2 is positioned adjacent to one side of the user's elbow when attached. The tension-diverting band 4 is adjacently connected to the joint-receiving sling 1, along the second lengthwise edge 12. Additionally, the second adjustable cuff 3 is adjacently connected to the tension-diverting band 4, opposite to the joint-receiving sling 1. Consequently, the tension-diverting band 4 is able to transfer forces, placed on the joint-receiving sling 1 by the external exercise equipment, away from the joint-receiving sling 1 and into the second adjustable cuff 3. Further, the tension-diverting band 4 and the second adjustable cuff 3 are positioned adjacent to the user's joint, opposite to the first adjustable cuff 2. Accordingly, the present invention is able to function as a brace that enables the forces generated by the external exercise equipment to be supported the user's forearm and upper arm. Thus positioned, the present invention is optimally situated to facilitate reducing the tension placed on the user's shoulder while exercising. The tension is reduced relative to the same exercise being performed with the external exercise equipment being grasped in the user's hand.

Figure 2:
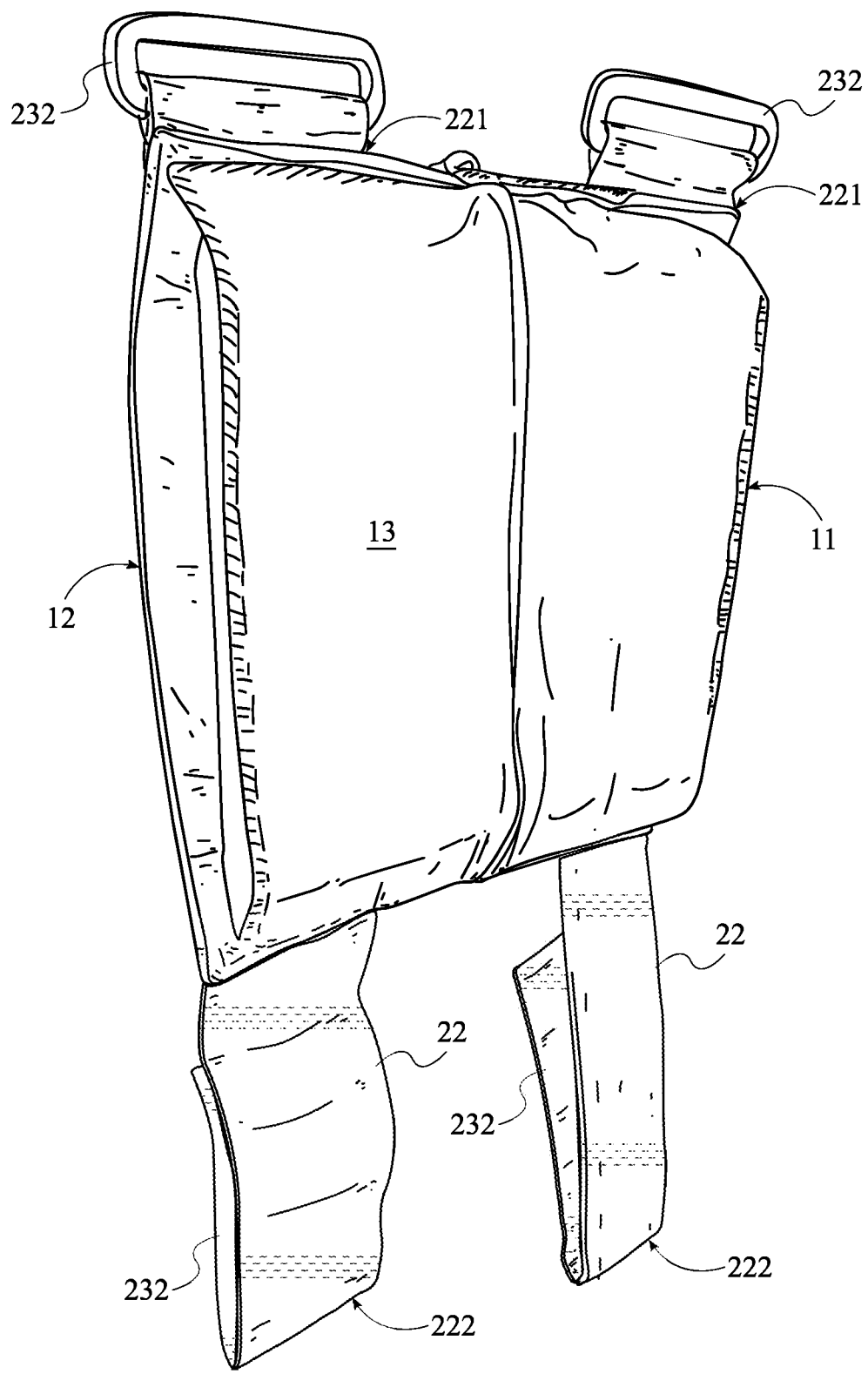
FIG. 2 is a rear perspective view of the present invention.

Referring to FIG. 1, FIG. 2, and FIG. 7, as described above, the present invention is designed to reduce the strain placed on the user's joint while performing strenuous activities. To that end, the present invention further comprises a padded liner 13. The padded liner 13 is a section of deformable material. Additionally, the padded liner 13 is adjacently connected to the joint-receiving sling 1, opposite to the first cuff and the tension-diverting band 4. As a result, the padded liner 13 forms a soft surface, against which the user's joint presses when the present invention is in use. Further, the padded liner 13 is designed to reduce discomfort felt by the user while performing strenuous activities. As a separate strain-reducing provision, a width 21 of the first adjustable cuff 2 is less than a width 31 of the second adjustable cuff 3. Accordingly, the first adjustable cuff 2 and the second adjustable cuff 3 can be positioned on the most advantageous sides of the user's joint. For example, when the present invention is affixed to the user's elbow, the first adjustable cuff 2 is wrapped around the user's upper arm. Because of the reduced width 21 of the first adjustable cuff 2, the present invention is able to rest comfortably beneath the user's bicep. Further, the larger width 31 of the second adjustable cuff 3 facilitates dispersing the forces being transferred by the tension-diverting band 4. In an alternative embodiment of the present invention, a second tension-diverting band 4 is mounted in between the first adjustable cuff 2 and the joint-receiving sling 1. In this embodiment the second tension-diverting band 4 functions to transfer forces from the joint-receiving sling 1 into the first adjustable cuff 2.

Figure 3:
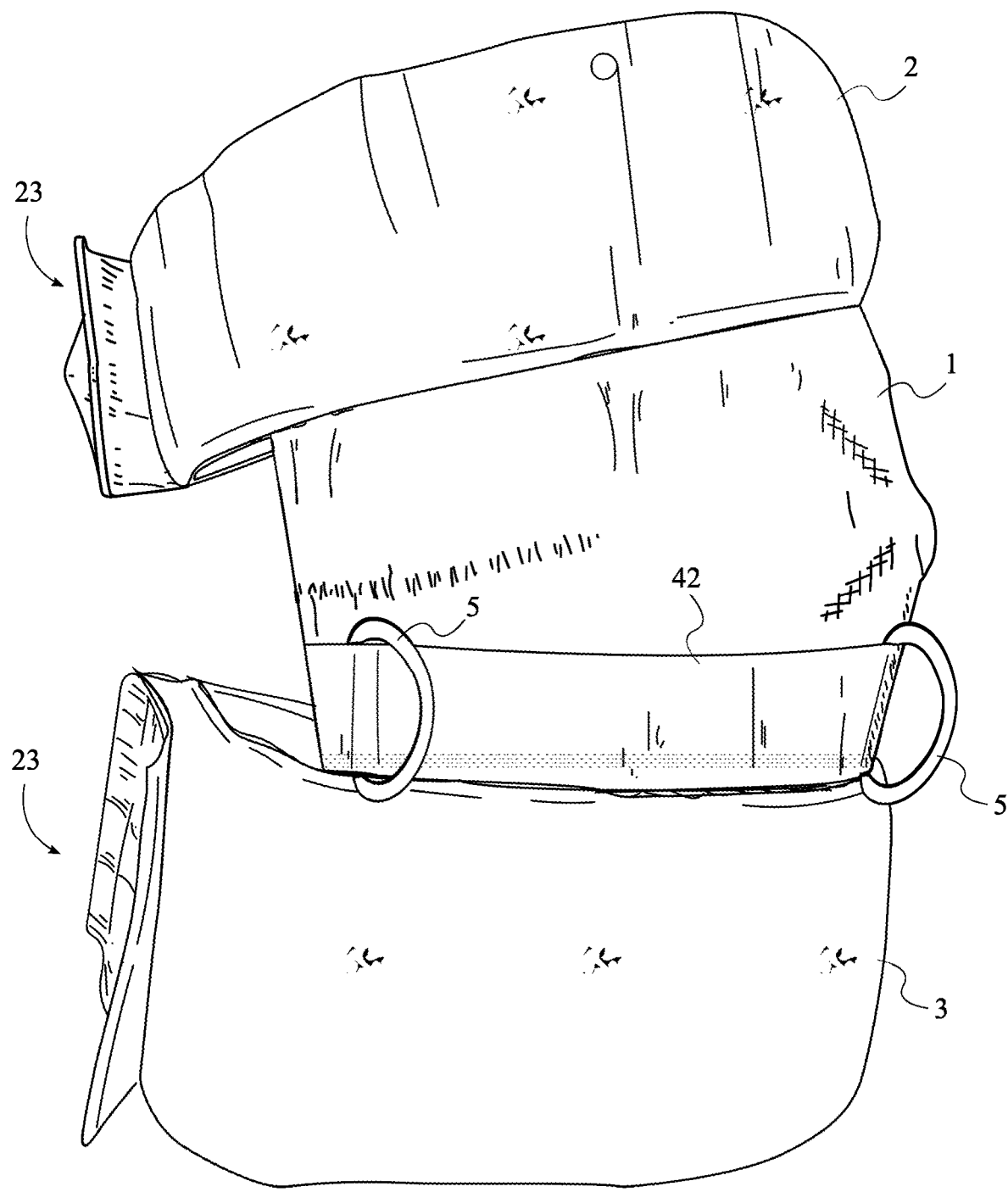
FIG. 3 is a left-side view of the present invention when the adjustable fastener is engaged.
Figure 4:
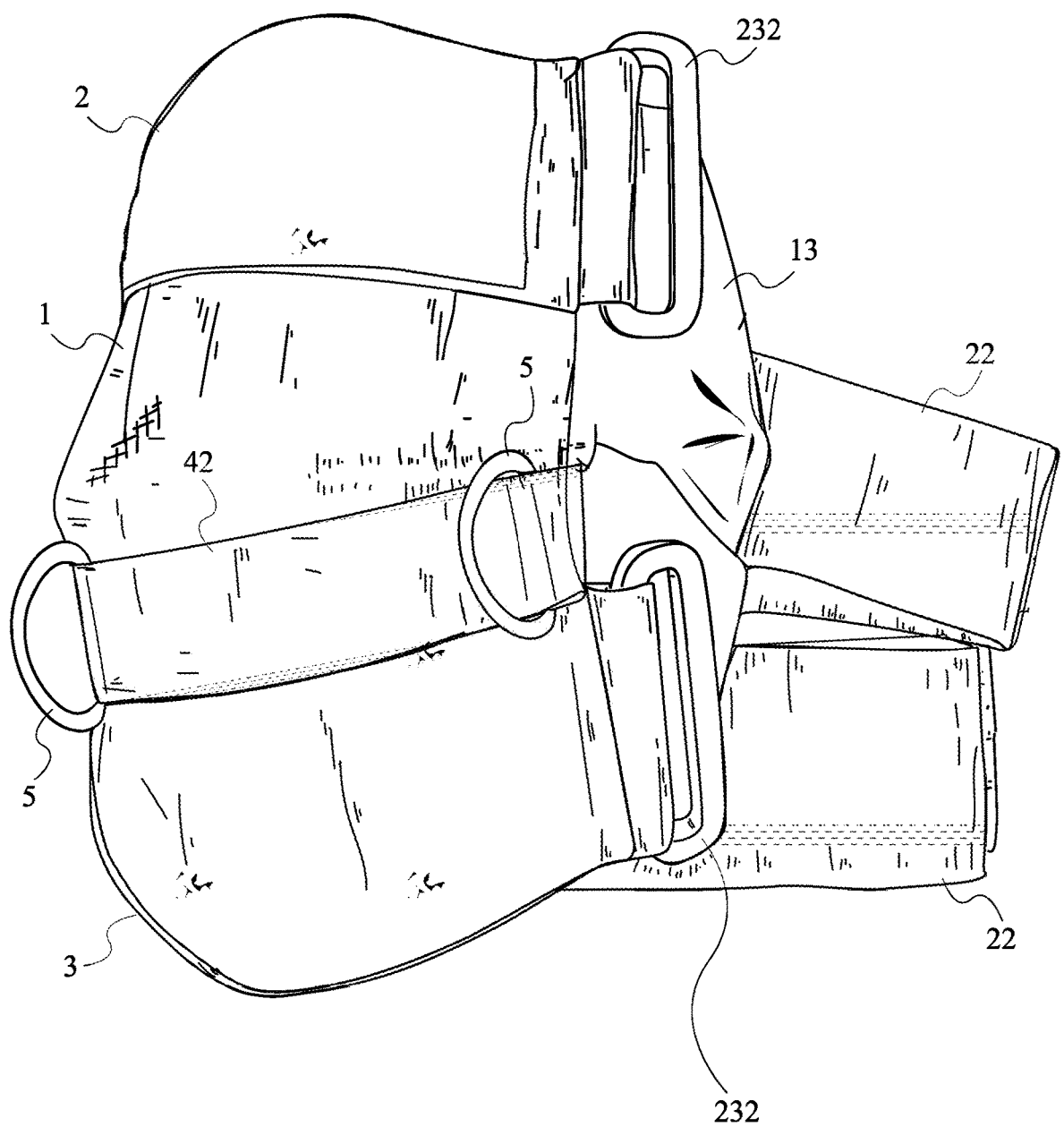
FIG. 4 is a right-side view of the present invention when the adjustable fastener is disengaged.
Figure 5:
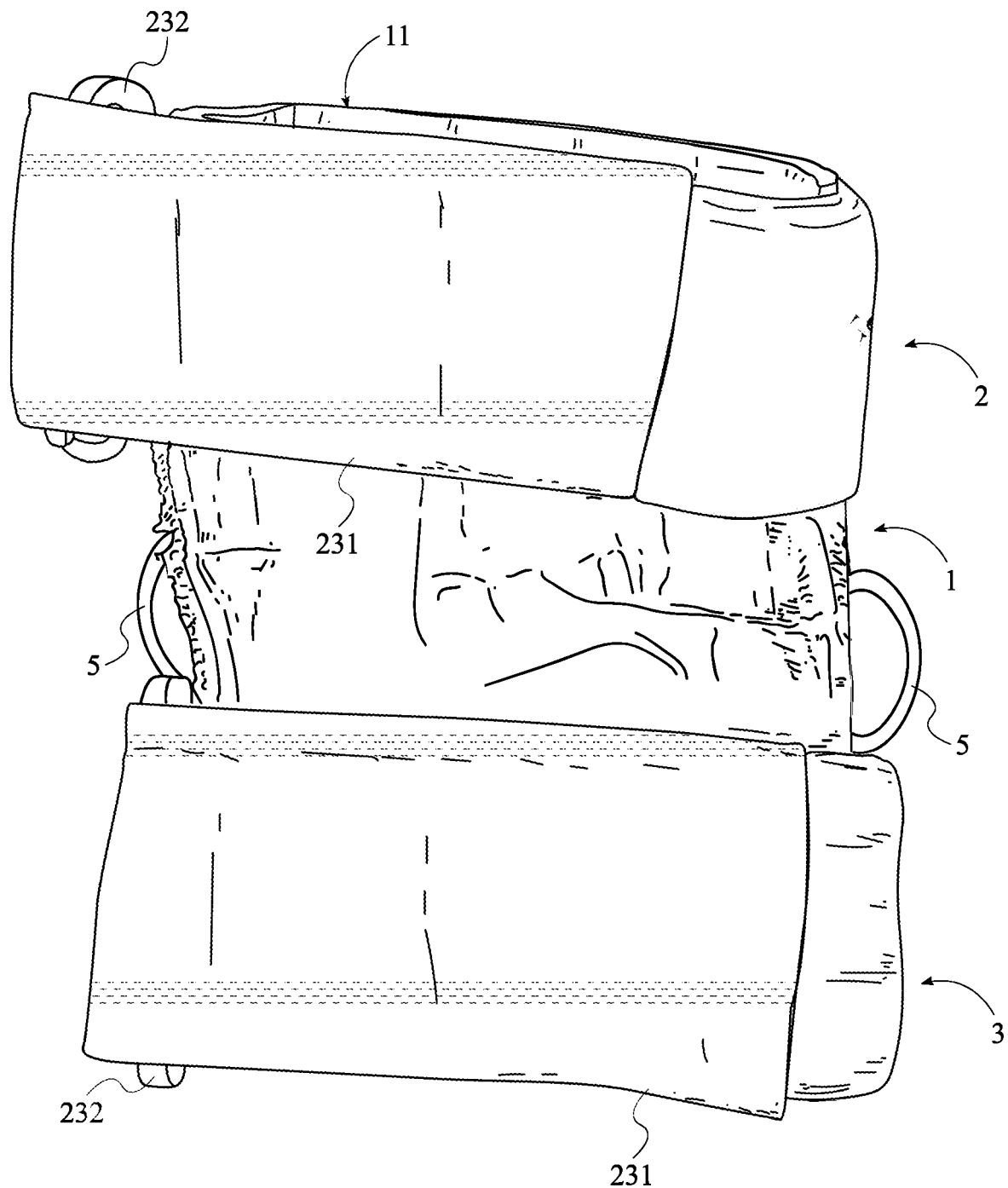
FIG. 5 is a rear perspective view of the present invention when the adjustable fastener is engaged.

Referring to FIG. 1 and FIG. 3, preferably, the first adjustable cuff 2 is constructed identically to the second adjustable cuff 3. That is, the first adjustable cuff 2 and the second adjustable cuff 3 each comprise a support strap 22 and an adjustable fastener 23. The adjustable fastener 23 is connected in between a first end 221 of the support strap 22 and a second end 222 of the support strap 22. Consequently, the user is able to affix the present invention around a joint by wrapping the first end 221 and the second end 222 around the user's arm and then connecting the two ends with the adjustable fastener 23. The adjustable fasteners 23 are designed to enable the user to increase or decrease the lengths of the first adjustable cuff 2 and the second adjustable cuff 3. Thus, facilitating attaching the present invention to users of varying shape and size. Preferably, the adjustable fastener 23 is a belted system that can be lengthened or adjusted as desired. Specifically, the adjustable fastener 23 comprises a hook-and-loop strap 231 and a buckle 232. The hook-and-loop strap 231 is a strap that has a section of hooked material and a section of looped material. The section of hooked material is designed to be mated to the section of looped material to form a hook-and-loop fastener. As described above, the adjustable fastener 23 is designed to function as a detachable fastening system that connects the first end 221 to the second end 222. To accomplish this, the hook-and-loop strap 231 is terminally connected to the first end 221. Additionally, the buckle 232 is adjacently connected to the second end 222. Further, the hook-and-loop strap 231 engages through the buckle 232. As a result, the user is able to move the buckle 232 along the length of the hook-and-loop strap 231 and then mate the section of hooked material to the section of looped material. Thus, enabling the user to increase or decrease the length of the support strap 22, which enables the user to adjust the fit of the first adjustable cuff 2 and the second adjustable cuff 3 around the joint.

Figure 8:
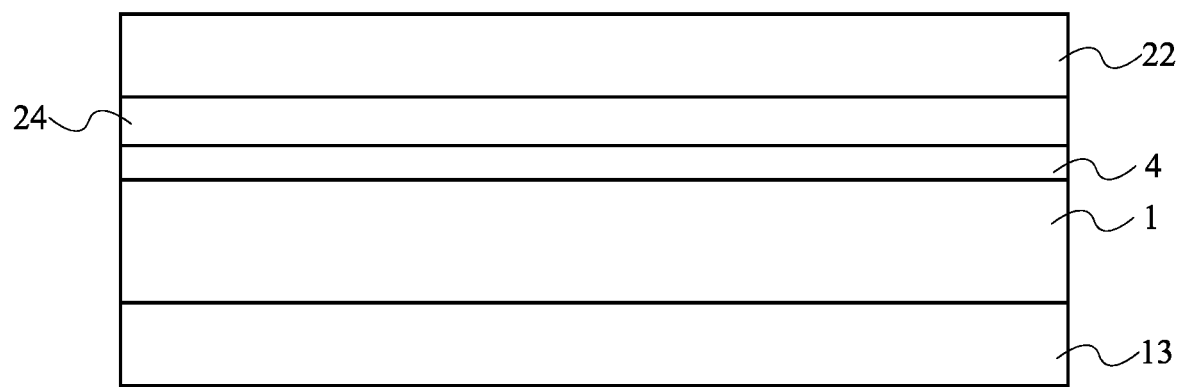
FIG. 8 is a block diagram of the present invention illustrating the arrangement of multiple stacked layers of material.
Figure 9:
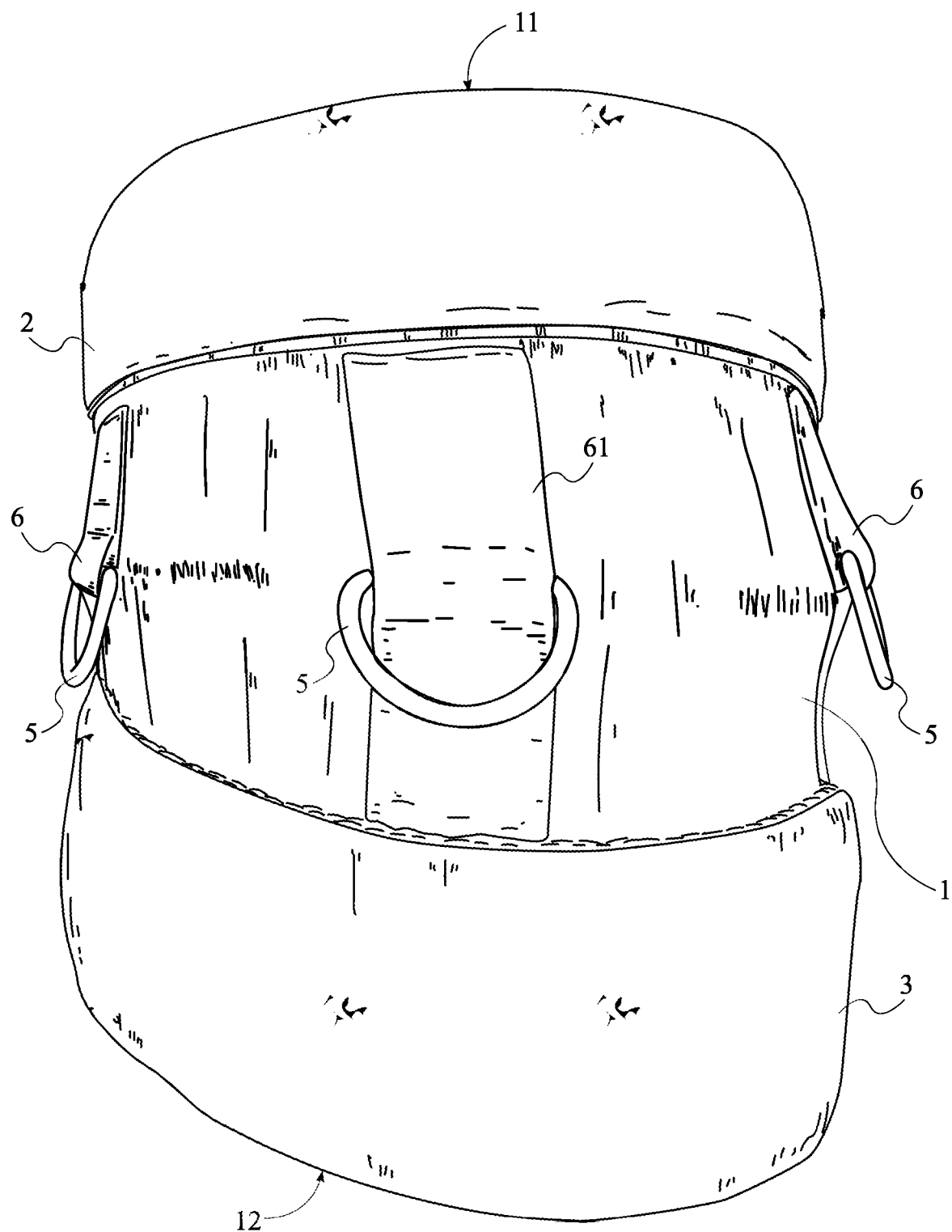
FIG. 9 is a front perspective view of an alternative embodiment of the present invention.

Referring to FIG. 1 and FIG. 8, the present invention is designed to prevent injury, rehabilitate joints, and reduce the discomfort experienced by the user while performing strenuous activities. To that end, the first adjustable cuff 2 and the second adjustable cuff 3 each further comprise a padding strip 24. The padding strip 24 is superimposed onto the support strap 22. Additionally, the padding strip 24 is positioned in between the support strap 22 and the joint-receiving sling 1. Thus positioned, the padding strip 24 further increases the user's overall comfortlevel while exercising.

Referring to FIG. 6 and FIG. 7, in addition to reducing joint strain and discomfort, the present invention is designed to enable the user to perform unique strength training and rehabilitative exercises. To facilitate this, the present invention further comprises a plurality of anchor points 5. Each of the plurality of anchor points 5 is a fastening mechanism that enables the external exercise equipment to be mounted onto the tension-diverting band 4. Additionally, the tension-diverting band 4 comprises a support portion 41 and a mounting portion 42. Further, the support portion 41 is positioned adjacent to the mounting portion 42. Accordingly, the tension-diverting band 4 is split into two distinct areas, each of which performing a unique function. The second adjustable cuff 3 is adjacently connected to the support portion 41 so that the forces generated by the external exercise equipment can be distributed among the joint-receiving sling 1, the first adjustable cuff 1, and the second adjustable cuff 3 where the forces are then redistributed across parts of the user's body that are adjacent to the joint. The plurality of anchor points 5 is mounted onto the mounting portion 42. Additionally, the plurality of anchor points 5 is distributed across the mounting portion 42. Consequently, the user is able to mount the external exercise equipment to the present invention by attaching the external exercise equipment to the plurality of anchor points 5. Preferably, the present invention is designed with three anchor points. The first anchor point is positioned anterior to the elbow. The first anchor point is positioned posterior to the elbow. The first anchor point is positioned lateral to the elbow. Thus positioned, the plurality of anchor points facilitates performing a wide variety of strength training and rehabilitative exercises. Further, any additional forces generated by the external exercise equipment are not directly applied to the user's elbow and are redirected toward the upper arm and forearm. The plurality of anchor points 5 allows for multiple resistance bands or cables to be used during strength-training.

Referring to FIG. 7, in a separate alternative embodiment, the present invention makes use of multiple connective straps to enable the external exercise equipment to be attached to the joint-receiving sling 1. Specifically, this separate embodiment further comprises a plurality of support webbings 6. Preferably the plurality of the plurality of support webbings 6 and the tension-diverting band 4 are constructed using elastic materials. Additionally, the plurality of support webbings 6 is connected in between the first adjustable cuff 2 and the second adjustable cuff 3. Thus connected, the plurality of support webbings 6 augments the tension redistribution functionality of the tension-diverting band 4. Relatedly, each of the plurality of anchor points 5 is mounted onto a corresponding webbing 61 from the plurality of support webbings 6. Accordingly, the external exercise equipment can be mounted onto the present invention by being attached to the plurality of anchor points 5.

Although the invention has been explained in relation to its preferred embodiment, it is to be understood that many other possible modifications and variations can be made without departing from the spirit and scope of the invention as hereinafter claimed.

Supplemental Descriptions of the Present Invention

The present invention is able to maximize tension and increase the range of motion during certain exercises that may be prohibited by large weights or improper form, thus working the upper body via the shoulder joint. The main body of the present invention comprises an upper hook and loop cinch strap, a base layer of neoprene with nylon backing, a thin layer of spandex for added comfort for the inner arm which also aids in maintaining of the overall shape, a plurality of rings sewn on to nylon webbing for increased durability, and a lower hook and loop cinch strap. The present invention is positioned onto the user's elbow, however various other embodiments may be created for different joints of the human body, thus not limiting the concepts disclosed in the design to one application. Furthermore, the present invention is designed to be adjustable through the upper and lower cinch traps allowing the user to a "one size fits all" arrangement to allow individuals to cater to their own specific needs in accordance to overall elbow diameter.

The present invention aims to be simple and easy enough for any individual to install themselves. The user will be able to position their arm inside the brace, position the rings into their designated areas, and tighten the upper strap and lower straps to securely brace the elbow joint. The simplicity of the design allows for an individual to not only secure the brace, but to allow an easy transition of the connecting resistance band/cable to another ring. The location of the rings being in three specific locations (anterior, lateral and posterior) allows for the simplistic understanding of how to go through the optimal range of motions of the glenohumeral joint. Simply attach a resistance band or cable one of the rings, posterior ring per say, and move your arm in the motion of which is in the exact opposite from where the force is being applied from. With little to no conscious understanding of the musculoskeletal system, an individual can perform a plethora of exercises by simply repositioning the elastic band or cable onto one of the three designated rings and moving away from the area of resistance. This will allow for the greater chance of individuals undergoing rehabilitation therapy to do more at-home workouts, improving their quality of life and speed in which an individual can recover.

The upper strap is positioned is concentrically around the user's triceps, proximal to the shoulder. The upper strap further comprises a support band, a hook and loop fastener, sewn onto the base neoprene layer. The hook and loop fastener allow individuals to secure the upper strap to their arm, however the present invention is not limited by these options, and other attachment methods may be used. In addition, a thin spandex layer is positioned on the interior wall of the neoprene base to maintain an adequate comfort level for the users and maintain relative structure. The support band provides enough backing resistance to ensure the present invention is able to withstand the repetitive motions that occur during rigorous exercising. Initially a layer of nylon webbing is sewn onto the neoprene layer to provide the substantial strength needed to sew individual layers of nylon in order to place the D-rings in a secured location. Three D-rings are secured in their respective anterior, lateral, and posterior locations.

The attachment rings allow the user to connect resistance to a set of predetermined locations in which the individual can perform a magnitude of different exercises to engage all muscles respectively. In the current embodiment, the plurality of rings is shaped to resemble the letter D, however the present invention is not limited to this option. Generally known as D-rings, this type of hardware is used commonly used to attach cables/elastic bands using straps. The plurality of rings allows the user to maintain the range of motion due to their close proximity to the shoulder joint, common form malfunctions occur when an individual bends their elbow joint to a degree when using a much more distal application of resistance located at the hand, compromising the degree of motion of which the shoulder joint can move in respect to the improper posture and technique performed. Improper technique and the substantial amount of torque applied which can occur utilizing a hand grip can be extremely damaging to one's shoulder joint.

Various materials may be used when constructing the plurality of rings, however in the current embodiment the plurality of rings is manufactured out of metal to ensure, the present invention is able to withstand high tensile forces that may occur during use. Depending on the type of exercise elastic cables may be attached to the plurality of rings, allowing the user to apply the desired tensile resistance. The lower strap resembles the upper strap in design and purpose, therefore it also comprises the support band, with the hook and loop attachment sewn to the base neoprene. The lower strap is concentrically positioned around the user's forearm distal from the shoulder joint and secured into place by fastening the hook and loop attachment. The present invention allows the user to utilize a plurality of tensile angles and provide the ability to contract various muscles of the body, without direct contact or utilization of the hand or wrist. The present invention aims to maintain the full range of motion for the user, while providing an alternative for a comprehensive shoulder and upper body workout regimens.

What is claimed is:

1. A multifunctional therapeutic workout enhancement brace comprising:
    a joint-receiving sling;
    at least one first adjustable cuff;
    at least one second adjustable cuff;
    at least one tension-diverting band;
    the joint receiving sling comprising a first lengthwise edge and a second lengthwise edge;
    the first lengthwise edge being positioned opposite to the second lengthwise edge across the joint-receiving sling;
    the first adjustable cuff being connected to the joint-receiving sling, along the first lengthwise edge;
    the tension-diverting band being connected to the joint-receiving sling, along the second lengthwise edge;
    the second adjustable cuff being connected to the tension-diverting band, opposite to the joint-receiving sling;
    a padded liner;
    the padded liner being connected to the joint-receiving sling, opposite to the first adjustable cuff and the tension diverting band;
    the first adjustable cuff comprising a first support strap, a first adjustable fastener and a first padding strip;
    the first adjustable fastener being connected in between a first end of the first support strap and a second end of the first support strap;
    the first padding strip being superimposed onto the first support strap;
    the first padding strip being positioned in between the first support strap and the joint-receiving sling;
    the second adjustable cuff each comprising a second support strap, a second adjustable fastener and a second padding strip;
    the second adjustable fastener being connected in between a first end of the second support strap and a second end of the second support strap;
    the second padding strip being superimposed onto the second support strap;
    the second padding strip being positioned in between the second support strap and the tension-diverting band;
    a plurality of anchor points;
    the tension-diverting band comprising a support portion and a mounting portion;
    the support portion being positioned adjacent to the mounting portion;
    the second adjustable cuff being connected to the support portion;
    the plurality of anchor points being mounted onto the mounting portion; and
    the plurality of anchor points being distributed across the mounting portion.

2. The multifunctional therapeutic workout enhancement brace as claimed in claim 1 comprising:
    a width of the first adjustable cuff being less than a width of the second adjustable cuff.

3. The multifunctional therapeutic workout enhancement brace as claimed in claim 1 comprising:
    the first adjustable fastener comprising a first hook-and-loop strap and a first buckle;
    the first hook and loop strap being terminally connected to the first end of the first support strap;
    the first buckle being connected to the second end of the first support strap; and
    the first hook and loop strap engaging through the first buckle;
    the second adjustable fastener comprising a second hook-and-loop strap and a second buckle;
    the second hook and loop strap being terminally connected to the first end of the second support strap;
    the second buckle being connected to the second end of the second support strap; and
    the second hook and loop strap engaging through the second buckle.

4. The multifunctional therapeutic workout enhancement brace as claimed in claim 1 comprising:
    a plurality of support webbings;
    the plurality of support webbings being connected in between the first adjustable cuff and the second adjustable cuff; and
    each of the plurality of anchor points being mounted onto a corresponding webbing from the plurality of support webbings.

* * * * *